United States Patent [19]

Kitahara et al.

[11] Patent Number: 4,927,808

[45] Date of Patent: May 22, 1990

[54] γ-L-GLUTAMYL-L-CYSTEINE ETHYL ESTER AND PHARMACEUTICAL COMPOSITIONS CONTAINING THE SAME AS AN EFFECTIVE INGREDIENT

[75] Inventors: Shigehisa Kitahara, Hino; Akira Ohtsu, Ohme; Katsuhiko Fujii, Hachioji, all of Japan

[73] Assignee: Teijin Limited, Osaka, Japan

[21] Appl. No.: 180,868

[22] PCT Filed: Jul. 7, 1987

[86] PCT No.: PCT/JP87/00475

§ 371 Date: Mar. 7, 1988

§ 102(e) Date: Mar. 7, 1988

[87] PCT Pub. No.: WO88/00182

PCT Pub. Date: Jan. 14, 1988

[30] Foreign Application Priority Data

Jul. 7, 1986 [JP] Japan ................................. 61-157798
Mar. 11, 1987 [JP] Japan ................................. 62-54229

[51] Int. Cl.$^5$ ........................ A61K 37/02; C07K 5/06; C07K 5/10
[52] U.S. Cl. ........................................ 514/19; 514/18; 530/330; 530/331; 560/147
[58] Field of Search ................... 514/19, 18; 530/331, 530/330; 560/147

[56] References Cited

U.S. PATENT DOCUMENTS 4,596,775  6/1986  Kimura et al. .................. 435/253
4,598,046  7/1986  Kimura et al. .................. 435/849
4,710,489  12/1987  Meister ............................. 530/331

FOREIGN PATENT DOCUMENTS 583262  9/1959  Canada ............................. 560/147

OTHER PUBLICATIONS

Flohe et al., The Identity of Glutatione Peroxidase from Erythocytes and Liver of the Rat, Z. Klin, Chem. 4, Klin Biochem. vol. 8, (1970), pp. 149–155.

Anderson et al., Glutathione Monoethyl Ester: Preparation, Uptake by Tissues, and Conversion to Glutathione, Arch. Biochem. Biophys., vol. 239, No. 2, pp. 538–548.

Primary Examiner—Lester L. Lee
Attorney, Agent, or Firm—Sughrue, Mion, Zinn, Macpeak & Seas

[57] ABSTRACT

γ-L-glutamyl-L-cysteine ethyl ester which has an activity to increase glutathione levels in tissues and a drug for treating liver diseases, cataracts, and kidney diseases containing it as the effective ingredient.

5 Claims, 4 Drawing Sheets

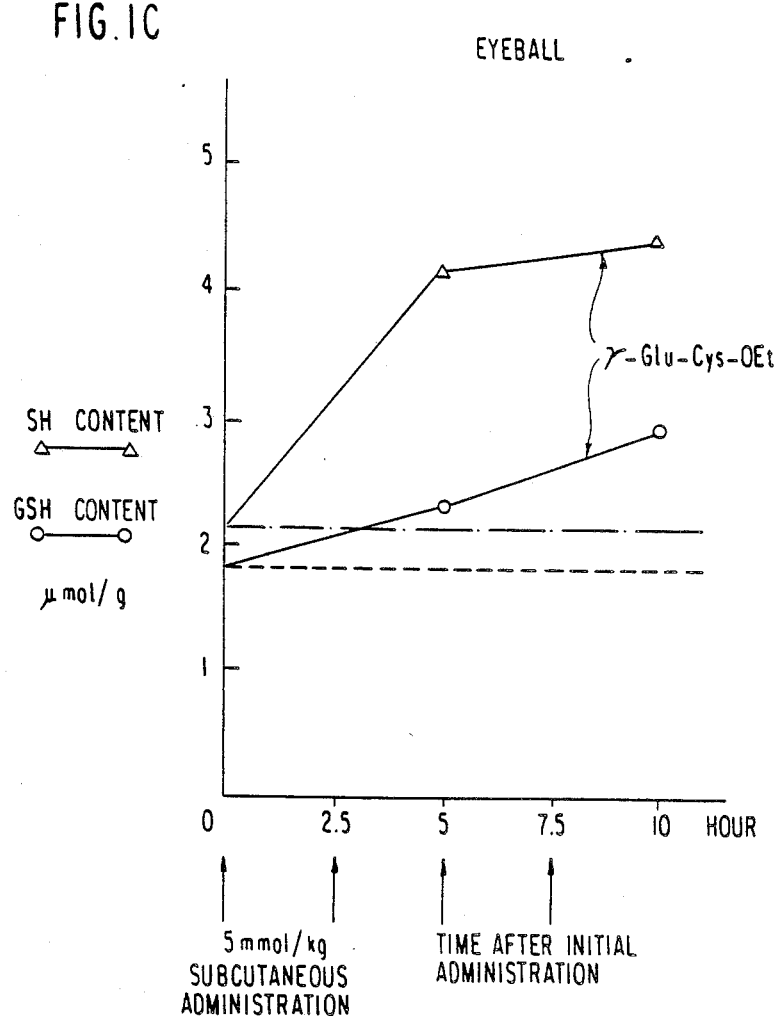

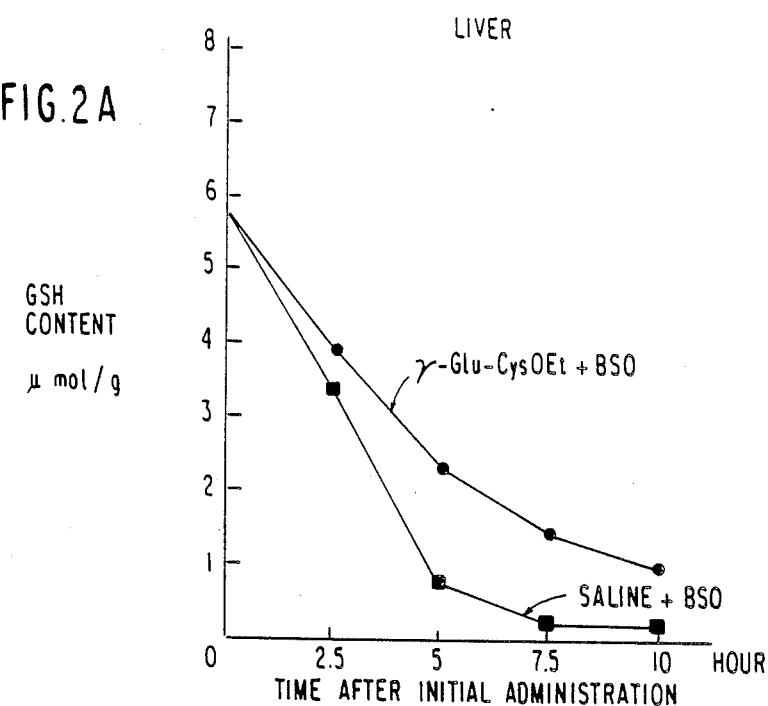
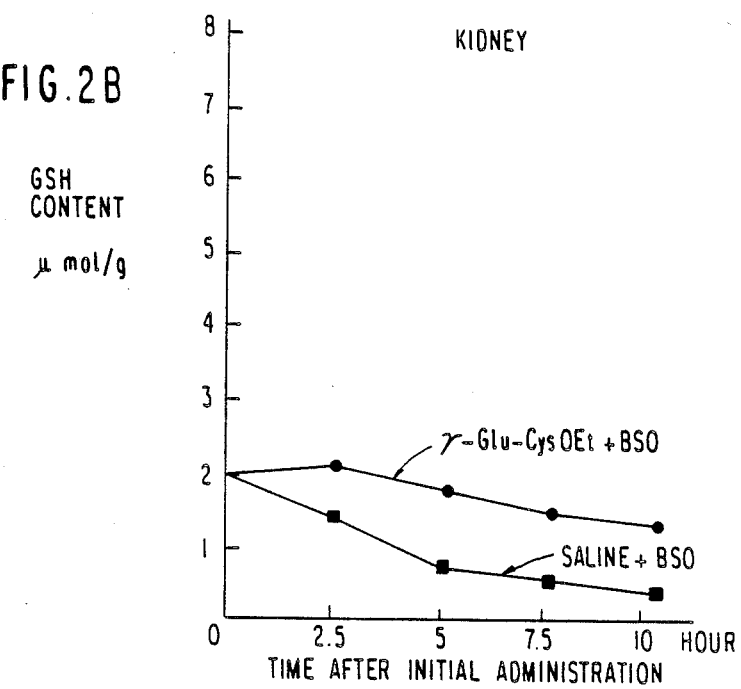

γ-L-GLUTAMYL-L-CYSTEINE ETHYL ESTER AND PHARMACEUTICAL COMPOSITIONS CONTAINING THE SAME AS AN EFFECTIVE INGREDIENT

TECHNICAL FIELD

The present invention relates to γY-L-glutamyl-L-cysteine ethyl ester and agents to increase the tissue glutathione levels, medicines for liver diseases, drugs for cataract, and medicines for kidney diseases, which contain the same as an effective ingredient.

TECHNICAL BACKGROUND

Glutathione is present in almost all biological tissues as a major intracellular reducing agent and plays important roles in catalysis, metabolism, transport and protection of cells. To be particular as to the protection of cells, glutathione displays said function (1) by reductively destorying reactive oxygen compounds and free radicals with the acid of glutathione peroxidase or (2) by reacting with intracellular toxic compound with the aid of glutathione-S-transferase and the reaction product being excreted out of the cells as a glutathione conjugate, thus playing roles in antioxidation, detoxication, protection against radiation injury, and increasing resistance to temperature, etc.

Therefore, when the tissue content of glutathione has decreased due to diseases or aging, the tissue becomes liable to suffer injuries. It is important for the restoration of lost cellular functions to decreased tissue glutathione levels to the normal value and it is also generally regarded that the cellular protective function can be further enhanced by increasing the tissue glutathione even in case of a normal cell. Actually it has also been reported that glutathione and several kinds of thiol compounds were used effective in protecting against mutagenic and carcinogenic substances and further in reducing the tumor size of the animal liver caused by from said malignant substances.

However, there are problems that half life of glutathione in blood is short (several minutes) and administration of glutathione itself is not so useful in increasing tisse glutathione. It is considered that this is due to the facts that glutathione itself can not be taken efficiently into cells, and exogenously supplied glutathione must be once degraded to its constituent peptide or amino acids, which are able to be transported and converted intracellularly to glutathione.

There have been several compounds that overcome problems above-mentioned and are proved to be superior to glutathione in increasing glutathione level of human lymphoma cells or animal tissues. 2-oxothiazolidine-4-carboxylate, γ-L-glutamyl-L-cysteine, and r-L-glutamyl-L-cysteinyl-glycine ethyl ester (glutathione monoethyl ester), etc. (for instance, Curr. Top. Cell. Regul., vol. 26, pp 383–394, 1985; Fed. Proc., vol. 43, pp 3031–3043, 1984).

Disclosure of the Invention

The present inventors have made a search for new compounds, which are effective for increasing glutathione in the tissue, by using a primary cultured hepatoxyte and found that γ-L-glutamyl-L-cysteine ethyl ester is effective in increasing glutathione of the liver cells; that especially in case where glutathione level is decreased by use of D,L-buthionine-sulfoximine, an inhibitor of glutathione synethsis, the addition of said glutamyl compound after the removal of the inhibitor makes the glutathione level recover at a remarkably high speed; that the glutathione level recovering effect of this compound is much superior to the compounds previously mentioned in the preceding paragraph; and that the compound prevents the necrosis of liver cells due to carbon tetrachloride treatment, thus achieved the present invention.

More particularly, this invention relates to γ-L-glutamyl-L-cysteine ethyl ester represented by the following formula

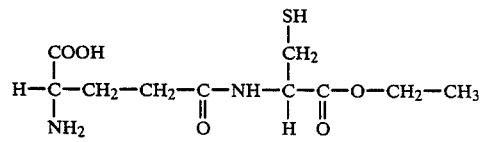

and agents to increase the tissue glutathione levels, medicines for liver diseases, drugs for cataract, and medicines for renal diseases, which contain the same as an effective ingredient.

The aforementioned formula indicates compound of reduced form and oxidized form of γ-L-glutamyl-L-cysteine ethyl ester (oxidized type dimer), which is a dimer comprising a disulfide linkage (-S-S-) formed by the dehydrogenation reaction caused between the two molecules of the compound of the aforementioned formula, is also included in the scope of this invention.

BRIEF DESCRIPTION OF DRAWINGS

FIGS. 1A, 1B and 1C are graphs showing how the compound of this invention acts to increase the tissue glutathione level upon administration to mice.

FIGS. 2A and 2B are graphs showing how the compound of this invention functions to mitigate the decrease of the tissue glutathione level when it is administered to mice which have been pretreated with L-buthionine sulfoximine.

BEST MODE OF CARRYING OUT THE INVENTION

Figure 1A:
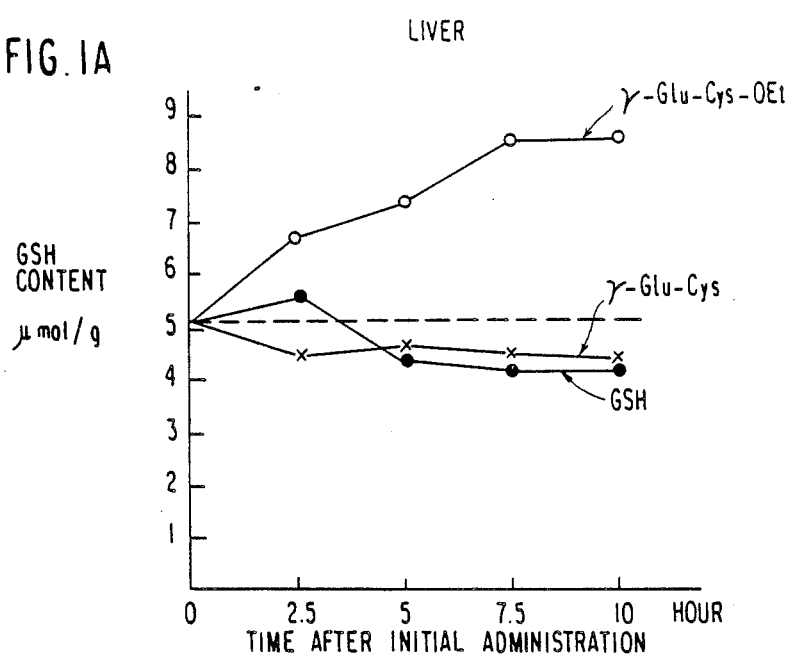

The compound of this invention is a derivative of a compound which has hitherto been publicly known as γ-L-glutamyl-L-cysteine methyl ester and can be synthesized organic chemically according to (1) a generally known method such as one reported by Flohé et al. in Z. Klin. Chem. u. Klin. Biochem., vol. 8, pp 149–155 (1970). The compound can also be synthesized (2) by monoethyl esterifying γ-L-glutamyl-L-cysteine by adopting a method of monoethyl esterification of glutathione reported by Anderson et al. in Arch. Biochem. Biophys., vol. 239, pp 538–548 (1985).

The present compound has a function to increase the tissues glutathione levels and is accordingly useful for the invigoration of various cells and prevention of necrosis. In view of the assumption that (1) the decrease of tissue glutathione level is the cause in part of adult diseases such as cataract, hypertension, arterio sclerosis, diabetes, gastric ulcer, cancer, renal diseases respiratory diseases, and diseases of brain and heart, the medicines of the present invention are effective for the prevention and therapy of the aforementioned diseases and further display marked curative effects as antitussive and expectorant agents, drugs for treating intoxication, various allergic diseases, cutaneous diseases, for preventing sunburn and radiation injury, and for increasing temperature resistivity and (2) are furthermore effective for remedy and prevention of liver troubles such as hepatitis, fatty liver, and liver cirrhosis. They also (3) have a detoxifying action for the renal toxicity resulting from the use of an anti-cancer agent and are therefore expected to be useful for the therapy and prevention of kidney diseases.

Also, in view of the fact that some kinds of thiol compounds are used for treating various diseases including liver troubles, intoxication, eye complaints, tussis and obstructive phlegm because of their antioxidative-reductive activity and action to bond with heavy metals due to their SH group, it may be reasonably expected that the present compounds, which have SH group, can display various remedial effects by themselves or as metabolites.

The compounds of this invention can be administered orally or parenterally such as intravenously, intramuscularly, subcutaneously, reactally, percutaneously, and eye dropping. As the dosage form for oral administration, tablet, pill, granule, powder, liquid preparation, suspension, and capsule may be mentioned.

As the method for preparing in the form of a tablet, it may be prepared according to the ordinary method in which excipients such as lactose, starch, and crystalline cellulose; binders such as carboxymethyl cellulose, methyl cellulose, and polyvinyl pyrrolidone; and disintegrators such as sodium alginate and sodium bicarbonate.

Pills, granules, and powders can also be prepared according to the ordinary method by use of glyserin ester such as tricaprylin and triacetin and alcohol such as ethanol. Capsules are prepared by filling gelatin capsules with granules, powder, or liquid preparation.

As the dosage form for intravenous, intramuscular, and subcutaneous administration, there are injections prepared in the form of an aqueous or nonaqueous solution. In preparing these injections, solvents such as isotonic sodium chloride solution, ethanol, and propylene glycol, and, if necessary, antiseptics and stabilizers are used.

For reactal administration, ordinary suppository made of gelatin soft capsule may be mentioned.

As the dosage form for percutaneous administration, ointments, for instance, may be mentioned. They are prepared according to the ordinary method.

Eye drops can be prepared by use of an nearly neutral buffer solution comprising, for instance, sodium bicarbonate, sodium bisulfite, and boric acid, and, if necessary, antiseptics, stabilizers, and osmotic pressure regulators may also be used.

When the compound of this invention is used as the agent for increasing the level of glutathione in the tissue, or remedy for treating liver diseases, cataract, and kidney troubles, the dosage is usually about 2 mg-20 g per day for an adult, though it varies depending upon the condition of the patient. It may be given orally or parenterally by divided administration ranging from 1 to 8 times a day.

The acute toxicity of the compound of this invention is very low as compared with the control compounds as shown in Example 10.

The invention will be further illustrated by the following examples.

EXAMPLE 1

Synthesis and purification of γ-L-glutamyl-L-cysteine ethyl ester and its oxidized form (i) Esterification After 250 ml of hydrogen chloride-containing ethanol (7N HCl-EtOH) was added to a dehydrated ethanol suspension (750 ml) containing 50 g (about 185 mmol) of γ-L-glutamyl-L-cysteine monohydrate, the mixture was stirred at room temperature for 1 hour. Upon addition of hydrogen chloride, the suspension turned to a solution. The reaction solution was then poured into ether (7.5 l) which had been cooled to 0° C. beforehand and the mixture was kept stirring for 2 hours to make the crystals precipitate. Thus obtained product was separated by filtration to give 48.4 g (83%) of γ-L-glutamyl-L-cysteine ethyl ester hydrochloride salt.

In the product thus obtained, 5-10% diester body is found existing. In order to obtain the desired compound in the form of a pure product, the hydrochloride slat should be neutralized with base such as amine and then purified by use of an ion-exchange resin.

(ii) Purification

A solution prepared by dissolving 45 g of the aforementioned γ-L-glutanyl-L-cysteine ethyl ester hydrochloride salt in 950ml of water was neutralized with aqueous ammonia and furthermore water was added to make the final volume of 1 l. The solution was made to pass continuously through BIO-RAD's AG 50 W ammonium-form column (50 ml of resin) and AG: acetate-form column 125 ml of resin), (both of) which had been wellwashed with water beforehand, and columes were finally washed with water equivalent to the volume of the columns. The eluate and the washings were put together and lyophilized to obtain 36 g of γ-L-glutamyl-L-cysteine ethyl ester. Its physical properties are as follows:

NMR (δppm, $D_2O$): 1.28 (3H, t, J=7.0 Hz), 2.16 (2H, m), 2.54 (2H, t, J=7.6 Hz), 3.00 (2H, m), 3.79 (1H, t, J=6.3 Hz), 4.26 (2H, q, J=7.0 Hz), 4.64 (1H, m)

When thus purified authentic sample was eluted on Waters' $C_{18}$ reversed phase column (4 mm×30 cm) at a flow rate of 1 ml/min, it showed the single peak of 4.7-minute retention time under the condition of acetonitrile (15%)/0.1% trifluoroacetic acid (85%) and the single peak of 7.4-minute retention time under the condition of acetonitrile (7.5%)/trifluoroacetic acid (92.5%).

(iii) Preparation of the oxidized form 7 g of γ-L-glutamyl-L-cysteine ethyl ester obtained in the preceding (ii) was dissolved in 50 ml of water. The solution was adjusted to pH7.4 with aqueous ammonia and after the addition of 10 mg of copper sulfate pentahydrate, air was blown thereinto overnight at room temperature.

The reaction solution was made to pass in succession through AG50W. ammonium form column 3 ml of resin) and AG1. acetate form column (3 ml of resin), which had been washed thoroughly with water, to remove copper sulfate therefrom and was lyophilized to obtain 6.30 g of γ-L-glutamyl-L-cystein ethyl ester of oxidized type dimer. Its physical properties are shown below.

NMR (δppm, $D_2O$): 1.4 (6H, t, J=7.0 Hz), 2.3 (4H, m), 2.55 (4H, m), 3.0~3.6 (4H, m), 3.9 (2H, m), 4.35 (4H, q, J=7.0 Hz), 4.9 (2H, m)

When this product was eluted on Shiseido's CAP-CELL PAK $C_{18}$ reversed phase column (4.6 mm×25 cm) at a flow rate of 1 ml/min under the mixed solvent condition of acetonitrile (20%)/0.1% trifluoroacetic acid (80%), the oxidized form eluated as single peak of 5.6-minute retention time and the reducing type eluated as the single peak of 4.2-minute retention time under the same conditions.

EXAMPLE 2

Action to increase the glutathione levels in the liver cells

Hepatocyte (sample) was prepared according to the method of Nakamura et al. published in the Protein, Nucleic Acid, and Enzyme, vol. 24, pp 55–76 (1981), partly adopting the method of Wang et al. reported in the In Vitro, vol. 21, pp 526–530 (1985). The liver of mice was purfused with 0.05% collagenase, and cells were collected by centrifugation, and were further centrifuged with percoll to collect the parenchymal hepatocytes. The obtained hepatocytes were dispersed in the Williams' medium E containing 10% bovine fetal serum, dexamethasone ($10^{-6}$M), insulin (1 μg/ml), and antibiotic, and were inoculated into the culture plate at a density of $1 \times 10^5$ cells/0.2 ml/cm². After unattached cells were removed once 1.5 hours later, the cultivation was continued at 37° C. in an atmosphere of 5% $CO_2$-95% air. The compound of this invention was added to the culture system to a concentration of 1 mM to measure the time lapsed changes of the cellular glutathione level according to the method reported by Owens and Belcher, Biochem. J., vol. 94, pp 705–711 (1965) and Tietze, Anal. Biochem., vol. 27, pp 502–522 (1969). The similar measurements were also made without the addition of the compound for comparison.

Table 1 shows time course change of the cellular glutathione level by relative values in which the value of 100 represent the value of the experiment before the addition of the compound.

TABLE 1

| | Compound | |
|---|---|---|
| Hours | Control (Not added) | γ-L-glutamyl-L-cysteine ethyl ester (1 mM) |
| 0 (before addition) | 100 | 100 |
| 0.5 | 100 | 140 |
| 1 | 100 | 170 |
| 2 | 100 | 200 |

To sum up the above table, it is apparent that the compound of this invention has an effect of increasing the glutathione levels in the liver cells.

EXAMPLE 3

Action to mitigate the decrease in glutathione levels in the liver cells when the compound of this invention is made to coexist with D,L-buthionine sulfoximine The cultured liver cells were cultured for 13 hours after the addition of D,L-buthionine sulfoximine to the concentration of 0.3 mM and the present compound to the concentration of 1 mM and then the levels of cellular glutathione were measured. The similar measurements were made on the controls in which nothing was added and in which D,L-buthionine sulfoximine only was added.

Table 2 shows the celular glutathione levels by relative values based on the value of 100 before the addition of the compounds.

TABLE 2

| | | 0 hour (before addition) | 13 hours later |
|---|---|---|---|
| Control (nothing added) | | 100 | 100 |
| D,L-buthionine sulfoximine | 0.3 mM | 100 | 17 |
| Coexistence of: | | | |
| D,L-buthionine sulfoximine | 0.3 mM | 100 | 30 |
| γ-L-glutamyl-L-cysteine ethyl ester | 1 mM | | |

It is apparent from the above table that the present compound has an effect to mitigate the decrease of the glutathione levels in the liver cells due to D,L-buthionine sulfoximine.

EXAMPLE 4

Action to promote the recovery of cellular glutathione levels and action to prevent the necrosis of liver cells resulting from the use of the present product in case where the cellular glutathione level is once decreased by use of D,L-buthionine sulfoximine and the inhibitor is removed thereafter.

D, L-buthionine sulfoximine was added to the cultured liver cells to a density of 0.5 mM and cultivation was carried on for 16 hours. D,L-buthionine sulfoximine was then removed and the compound of this invention and control compounds (equimolar mixture of glutamic acid, cysteine, and glycine; glutathione; glutathione monoethyl ester; γ-L-glutamyl-L-cysteine) were respectively added to each culture to a density of 1 mM and was followed by 2-hour cultivation. The changes of cellular glutathione levels were measured at that time. Thereafter the compounds studied were removed from the respective cultures whose culture media were then replaced with new ones containing carbon tetrachloride at a density of 0.5 μl/ml. After 1-hour cultivation, the action to prevent the necrosis of liver cells was examined by measuring the GPT activity of the respective culture supernatants and Trypan Blue staining test.

In Table 3, the changes of cellular glutathione levels are expressed by relative values based on the untreated value set at 100 and the action to prevent the necrosis of liver cells is indicated by the GPT activity of the culture supernatant and survival rate.

TABLE 3

| | Cellular glutathion level | GPT activity of culture supernatant (untill/ml) | Survival rate (%) |
|---|---|---|---|
| Control (not treated) | 100 | 3 | 100 |
| D,L-buthionine sulfoximine 0.5 mM (16 hours) | 1 | — | — |
| Liquid culture medium only, after the | 1.5 | 80 | 2 |

TABLE 3-continued

|  | Cellular glutathion level | GPT activity of culture supernatant (until/ml) | Survival rate (%) |
| --- | --- | --- | --- |
| removal of D,L-buthionine sulfoximine (2 hours) |  |  |  |
| Mixture of glutamic acid, cysteine, and glycine each 1 mM added | 5.5 | 70 | 5 |
| Glutathione 1 mM added | 10 | 60 | 10 |
| Glutathione monoethyl ester 1 mM added | 15 | 35 | 25 |
| γ-L-glutamyl-L-cysteine 1 mM added | 10 | 60 | 10 |
| γ-L-glutamyl-L-cysteine ethyl ester (of this invention) 1 mM added | 50 | 3 | 100 |

It is now apparent that γ-L-glutamyl-L-cysteine ethyl ester can recover the glutathione level of liver cells once decreased by D,l-buthionine sulfoximine much faster than the cases where the compound of this invention is not added or other control compounds mentioned hereinbefore are added and also displays the most excellent effect to prevent the necrosis of liver cells. It is, therefore, expected that the compound of this invention is effective for the therapy and prevention of liver diseases such as hepatitis, fatty liver, and liver cirrhosis.

EXAMPLE 5

Action to recover the glutathione levels of liver cells upon the removal of carbon tetrachloride and addition of the present compound after the cellular glutathione level was once decreased by carbon tetrachloride After carbon tetrachloride was added to the cultured liver cells at a concentration of 0.5 μl/ml, culture was continued for 1 hour. The culture had then its medium exchanged with a new liquid culture medium and also had the present compound added at a density of 1 mM. One hour later, the change of the cellular glutathione level was measured.

Table 4 shows the changes of the cellular glutathione level in terms of relative values based on the value of 100 before the carbon tetrachloride treatment.

TABLE 4

|  |  | Cellular glutathione level |
| --- | --- | --- |
| Control (not treated) |  | 100 |
| After treated with carbon tetrachlodie | (0.5 μl/ml) | 33 |
| No compound added after the removal of carbon tetrachloride |  | 13 |
| Addition of γ-L-glutamyl-L-cysteine ethyl ester after the removal of carbon tetrachloride, | 1 mM | 67 |

The present compound has an effect to recover the cellular glutathione levels which have been decreased by carbon tetrachloride.

EXAMPLE 6

Action to increase the tissue glutathione levels in case where the present compound is given to mice ICR male mice (9-day old) were subcutaneously given 2.5 mmol/kg of the compound of this invention (r-Glu-Cys OET) or control compounds (glutathione (GSH), γ-L-glutamyl-L-cysteine (r-Glu-Cys)) four times at 2.5-hour intervals. The mice were dissected and their livers and kidneys were removed before the administration and every 2.5 hour after the administration to have their glutathione (GSH) level determined. As for eyeballs, besides the determination of glutathione contents, the SH contents were also determined by the DTNB method upon administration of 5 mmol/kg of the present compound after the same procedure. The results are shown in FIGS. 1A, 1B and 1C.

Figure 1B:
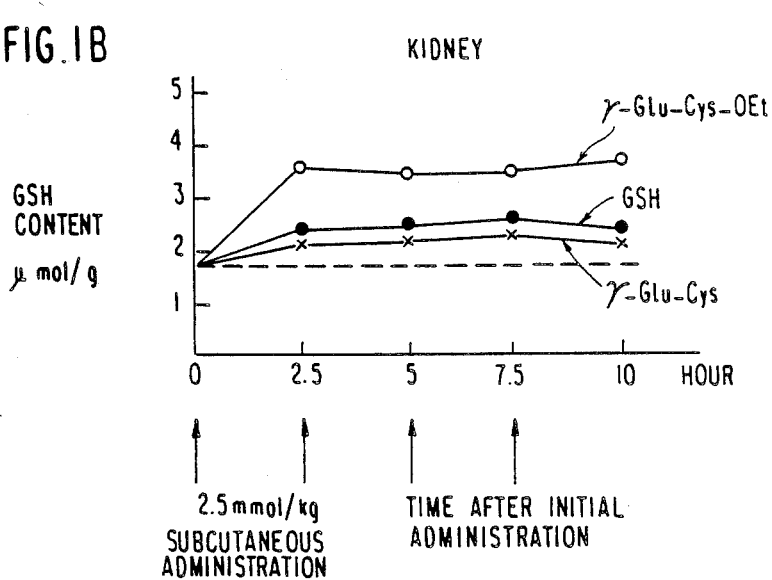

It is clearly shown in FIGS. 1A, 1B and 1C that the compound of this invention has far more excellent effect than glutathione and γ-L-glutamyl-L-cysteine in increasing the tissue glutathione levels of the liver (FIG. 1 (A)) and kidney (FIG. 1 (B)) even in case of animals. It is also seen that the compound has also an effect to improve the SH levels remarkably in addition to the aforementioned effect in case of eyeballs (FIG. 1 (C)).

EXAMPLE 7

Action to mitigate the decrease of tissue glutathione levels in case where the present compound and L-buthionine sulfoximine are alternately given to mice The compound of this invention was administered in the same way as Example 6, and L-buthionine sulfoximine (BSO) was administered likewise in dosage of 4 mmol/kg one hour after every administration of said compound. The contents of glutathione in the livers and kedneys were measured according to the methods described in Example 6 every 2.5 hours after the initial administration of the present compound. As controls, saline was administered in place of the present compound to take the similar measurements. FIGS. 2A and 2B shown the results.

It has been made apparent that the present compound has an effect to mitigate the decrease of tissue glutathione levels of the liver (FIG. 2A and kidney induced by L-buthionine sulfoximine, even in case of animal models (FIG. 2 (B)).

EXAMPLE 8

Figure 3A:
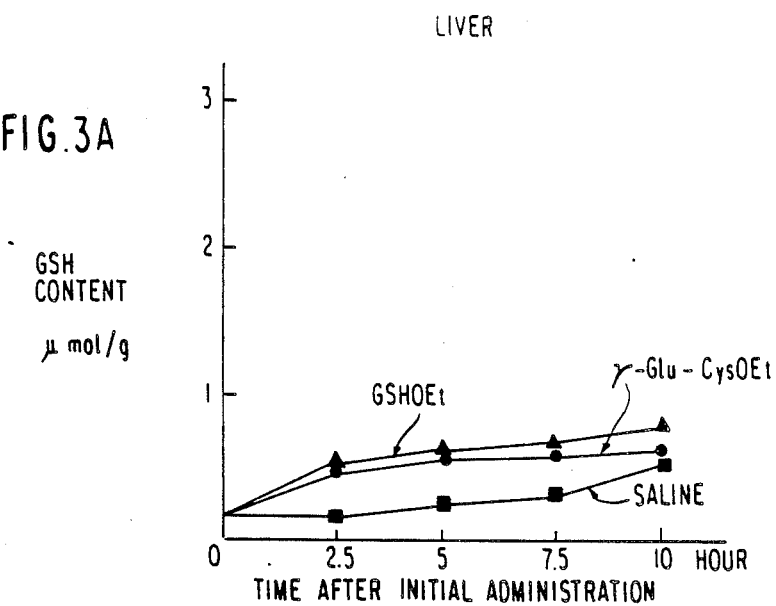
FIGS. 3A and 3B are graphs showing how the compound of this invention functions with regard to tissue glutathione levels when administered to mice 1 day after administering L-buthionine sulfoximine.

Action to promote the recovery of tissue glutathione levels in case where the present compound is administered to mice pretreated with L-buthionine sulfoximine ICR male mice (9-day old) were given L-buthionine sulfoximine in dosage of 4 mmol/kg four times at an interval of 2.5 hours to decrease their tissue glutathione levels beforehand. The next day, the mice were given subcutaneously 2.5 mmol/kg of the present compound or saline 4 times at an interval of 2.5 hours. Glutathione monoethyl ester (GSHOET) was also given likewise in dosage of 2.5 mmol/kg as a control. The contents of glutathione in the livers and kidneys were measured according to the methods described in Example 6. The results are shown in FIGS. 3A and 3B.

Figure 3B:
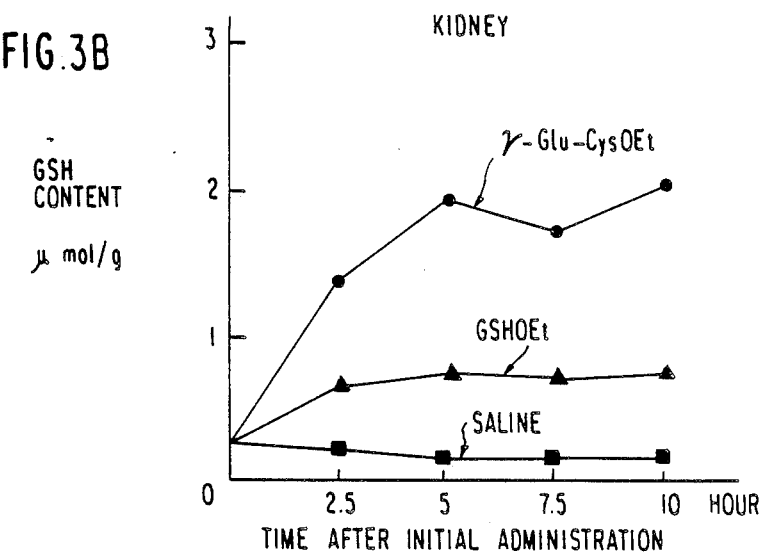

The present compound showed the same effectiveness as glutathione monoethyl ester in recovering the tissue glutathione levels of the liver (FIG. 3 (A)). With regard to the kidney (FIG. 3B, however, the present compound showed far more excellent effect in making the tissular glutathion level recover to the normal level as compared with glutathione monoethyl ester.

It is clear that, in cases of animal models too, the present compound has far more excellent effect of quickly recovering the tissue glutathione levels decreased by L-buthionine sulfoximine as compared to glutathione monoethyl ester, not to speak of a case where no treatment was made.

EXAMPLE 9

Protective effect of the present compounds (of reduced form and oxidized form) on experimentally developed cataract induced by L-buthionine sulfoximine Experimental cataract was prepared according to the method of Calvin et al., Science, vol. 233, pp 553–555 (1986). More particularly, L-buthionine sulfoximine was administered subcutaneously to the ICR male mice at a dose of 4 mmol/kg for 3 successive days from the 9th day to the 11th day after birth every 2.5 hours 4 times a day to cause cataract. The rate of cataractgenesis was determined on the 16th day after birth. The test compounds were also given subcutaneously for 3 days from the 9th day to the 11th day after birth 4 times a day 1 hour before the administration of L-buthionine sulfoximine and thereafter the test compounds studied only were subcutaneously given 4 times a day at an interval of 2.5 hours on the consecutive 12th and 13th days after birth and the protective effect of the test compound on cataract formation was examined on the 16th day after birth. As the control compounds, glutathione, glutathione monoethyl ester, and γ-L-glutamyl-L-cysteine were also examined.

Table 5 shows protective effect of the respective compounds studied on cataract formation.

The cataract development rate in the table means the ratio of the experimental animals developing cataract to all the animals examined (11 to 12 mice per group) and the cataractous eye rate means the ratio of cataractous eyes to the whole number of eyes examined.

TABLE 5

| Treatment | Dose of compound studied (mmol/kg) | Cataract development rate (%) | Cataractous eye rate (%) |
|---|---|---|---|
| Not treated | — | 0 | 0 |
| L-buthionine sulfoximine (4 mmol/kg) | — | 91.7 | 91.7 |
| L-buthionine sulfoximine + glutathione | 1.25 | 75.0 | 70.8 |
| L-buthionine sulfoximine + glutathione monoethly ester | 2.25 | 50.0 | 29.2 |
| L-buthionine sulfoximine + glutathione monoethyl ester | 1.25 | 50.0 | 41.7 |
| L-buthionine sulfoximine + γ-L-glutamyl-L-cysteine | 1.25 | 66.7 | 77.8 |
| L-buthionine sulfoximine + γ-L-glutamyl-L-cysteine ethyl ester (compound of this invention) | 2.50 | 0 | 0 |
| L-buthionine sulfoximine + γ-L-glutamyl-L-cysteine ethyl ester | 1.25 | 50.0 | 41.7 |
| L-buthionine sulfoximine + oxidized form γ-L-glutamyl-L-cysteine ethyl ester (compound of this invention) | 2.50 | 30.0 | 35.0 |

If is clear from the above table that the compounds of this invention (inducing reduced form and oxidized form) have a strong protective activity against experimental cataract induced by L-buthionine sulfoximine.

EXAMPLE 10

Acute toxicity of the present compound (mouse newborns)

Acute toxicity of the present compound was examined where it is administered according to the schedule of Example 9 and compared with there of controls, glutathione, glutathione monoethyl ester, and γ-L-glutamyl-L-cysteine. Table 6 shows the surviving rates of the animals after the ending of administration of the compounds studied.

When the present compound was given to the animals at a dosage of 2.5 mmol/kg, all the experimental animals survived, which shows that the compound is as almost equally safe as glutathione monoethyl ester and apparently has much more safety than glutathion or γ-L-glutamyl-L-cysteine. Also, the present compound showed an effect to mitegate suppressed increment of animals' body weight by the toxicity of BSO though such effect was not seen with glutathione or r-L-glutamyl-L-cysteine. It is, therefore, expected that, when the present compound is used in the treatment of cataract, it has high safety as compared with the control compounds.

TABLE 6

| Compound | Surviving rate (%) |
|---|---|
| L-buthionine sulfoximine (4 mmol/kg) | 100 |
| L-buthionine sulfoximine + glutathione (2.5 mmol/kg) | 50 |
| L-buthionine sulfoximine + glutathione (1.25 mmol/kg) | 100 |
| L-buthionine sulfoximine + glutathione monoethyl ester (2.5 mmol/kg) | 100 |
| L-buthionine sulfoximine + glutathione monoethyl ester (1.25 mmol/kg) | 100 |
| L-buthionine sulfoximine + γ-L-glutamyl-L-cysteine (2.5 mmol/kg) | 0 |
| L-buthionine sulfoximine + γ-L-glutamyl-L-cysteine (1.25 mmol/kg) | 75 |
| L-buthionine sulfoximine + γ-L-glutamyl-L-cysteine ethyl ester (2.5 mmol/kg) (of this invention) | 100 |
| L-buthionine sulfoximine + γ-L-glutamyl-L-cysteine ethyl ester (1.25 mmol/kg) (of this invention) | 100 |
| L-buthionine sulfoximine + oxidized form γ-L-glutamyl-L-cysteine ethyl ester (2.5 mmol/kg) (of this invention) | 100 |

EXAMPLE 11

Action to detoxify renal toxicity induced by cisplatin

Cisplatin was administered intraperitoneally to ICR male mice (5-week old) at a dose of 20 mg/kg. The present compound (2.5 mmol/kg) was intraperitoneally given to the mice at 2.5-hour intervals 4 times a day for 5 consecutive days including the day on which cisplatin was administered. The control groups were given saline instead of the present compound. The blood was collected one week after cisplatin administration to determine urea nitrogen levels in the blood serum (BUN). The result is shown in Table 7 (mean value of 10 mice per group). The present compound detoxified the renal disturbance activity of cisplatin seen with the increase of BUN.

TABLE 7

| Treatment | BUN (mg/dl) |
| --- | --- |
| Not treated (normal value) | 20.8 |
| Cisplatin + saline | 49.0 |
| Cisplatin + γ-L-glutamyl-L-cysteine ethyl ester | 35.7 |

We claim:

1. γ-L-glutamyl-L-cysteine ethyl ester expressed by the following formula or its dimeric oxidized form:

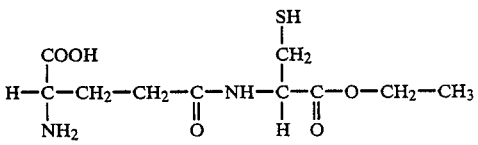

wherein said dimeric oxidized form is formed by dehydrogenation between two molecules of said γ-L-glutamyl-L-cysteine ethyl ester.

2. A pharmaceutical composition to increase tissue glutathione levels comprising γ-L-glutamyl-L-cysteine ethyl ester or its dimeric oxidized form as the effective ingredient, wherein said dimeric oxidized form is formed by dehydrogenation between two molecules of said γ-L-glutamyl-L-cysteine ethyl ester, in a pharmaceutically acceptable carrier.

3. A hepatotonic composition containing γ-L-glutamyl-L-cysteine ethyl ester or its dimeric oxidized form as the effective ingredient, wherein said dimeric oxidized from is formed by dehydrogenation between two molecules of said γ-L-glutamyl-L-cysteine ethyl ester, in a pharmaceutically acceptable carrier.

4. A pharmaceutical composition for treating cataracts containing γ-L-glutamyl-L-cysteine ethyl ester or its dimeric oxidized form as the effective ingredient, wherein said dimeric oxidized form is formed by dehydrogenation between two molecules of said γ-L-glutamyl L-cysteine ethyl ester, in a pharmaceutically acceptable carrier.

5. A pharmaceutical composition for treating kidney diseases containing γ-L-glutamyl-L-cysteine ethyl ester or its dimeric oxidized form as the effective ingredient, wherein said dimeric oxidized form is formed by dehydrogenation between two molecules of said γ-L-glutamyl-L-cysteine ethyl ester, in a pharmaceutically acceptable carrier.

* * * * *